(12) United States Patent  
Lovoi

(10) Patent No.: US 6,319,188 B1  
(45) Date of Patent: Nov. 20, 2001

(54) VASCULAR X-RAY PROBE

(75) Inventor: Paul A. Lovoi, Saratoga, CA (US)

(73) Assignee: Xoft microTube, Inc., Fremont, CA (US)

(*) Notice: Subject to any disclaimer, the term of this patent is extended or adjusted under 35 U.S.C. 154(b) by 0 days.

(21) Appl. No.: 09/299,304

(22) Filed: Apr. 26, 1999

(51) Int. Cl.$^7$ .................................................. A61N 5/00
(52) U.S. Cl. .............................................................. 600/3
(58) Field of Search ............................ 600/1, 3; 604/20, 604/21; 378/65

(56) References Cited

U.S. PATENT DOCUMENTS

| | | | |
|---|---|---|---|
| 5,090,043 | * | 2/1992 | Parker et al. ................. 378/65 X |
| 5,428,658 | * | 6/1995 | Oettinger et al. ................. 378/119 |
| 6,108,402 | * | 8/2000 | Chornenky ................. 37/65 X |

* cited by examiner

Primary Examiner—John P. Lacyk  
Assistant Examiner—Joseph A. Cadugan  
(74) Attorney, Agent, or Firm—Thomas M. Freiburger

(57) ABSTRACT

A vascular X-ray probe is formed of an optical fiber cable with a high voltage conductor embedded in the optical fiber and an external ground coating, feeding power to a small X-ray tube at the end of the cable. The optical fiber provides a conduit for optical radiation, preferably a laser beam, fed to a thermionic cathode mounted at the end of the light path, so that the laser beam heats the cathode causing it to emit electrons. An anode/X-ray target is opposite the cathode within the evacuated X-ray tube, and the ground lead is fed to the anode via an external ground coating over the tube. The X-ray tube is in preferred embodiments is less than 3 mm in diameter, and more preferably about 1.5 mm. In one embodiment the tube is formed directly in the end of the optical fiber cable, with the anode mounted on an exit window.

22 Claims, 6 Drawing Sheets

VASCULAR X-RAY PROBE

BACKGROUND OF THE INVENTION

The invention concerns treatment of vascular walls to prevent restenosis after balloon angioplasty and/or stent implantation, and particularly the invention concerns a catheter with an X-ray tube at its distal end, for performing such treatment.

As a treatment for coronary artery disease, balloon angioplasty, or percutaneous transluminal angioplasty has been used on an increasing basis. In a great number of cases, often estimated at up to 50 percent, restenosis occurs at the site where the angioplasty was administered. Restenosis is the re-closing of arteries after balloon angioplasty and/or stenting. The re-closing is caused by a hyperproliferative cellular response to the balloon and stent injuries. The scarring of the vessel can be sufficiently severe to obstruct blood flow through the vessel. As one type of countermeasure, stents have recently come into wide use, the stent being a metal, tubular vascular prosthesis which is implanted after angioplasty to mechanically hold the vessel lumen open. However, even with a stent in place, in-stent restenosis still tends to occur in more than 25 percent of cases.

Drugs have been suggested and tried for the purpose of preventing or limiting restenosis. These include heparin, dexamethasone and integralin, as well as others. These drugs have generally comprised anticoagulants and arterial smooth muscle proliferation inhibitors as well as agents to prevent aggregation of platelets. Catheters have been suggested for helping assure that the drug is applied directly to the site in question. Effective local application of such drugs is difficult and generally unproven as to effectiveness.

Radiation is known to be effective in reducing restenosis after angioplasty. This has been done using a radioactive isotope mounted on the tip of a catheter, emitting gamma or beta radiation, inserted into the vessel until the emitter is at the lesion location. Problems with the use of radioactive isotopes may include the need for a shielded operating room, with special care and handling of the radioactive sources and the catheter and problems of disposal; the effect of the radiation throughout the length of the blood vessel through which it is inserted, when only one particular site is desired to be irradiated; and inadequate control of the depth of penetration of the radiation from the isotope sources.

See, for example, U.S. Pat. No. 5,199,939 disclosing a catheter with a radioactive source for irradiating an angioplasty site to prevent restenosis.

U.S. Pat. Nos. 4,143,275, 5,153,900, 5,428,658, 5,422,926, 5,442,678, 5,452,720, 5,621,780, RE34,421, and PCT Publication WO 97/7740 all disclose X-ray devices for delivering radiation to remote positions in the body, including narrow passageways as small as blood vessels. Thus, these latter patents and publications describe radiation emitters which can be switched on and off, not involving use or handling of radioactive isotopes. Several of these patents describe probes with fiber optic cables leading to X-ray tubes, the fiber optic designed to carry light which activates a photo cathode in the tube. To date none of these proposed X-ray delivery devices has been built and effectively used in the human vascular system. Problems of X-ray absorption, sufficient power, lengthy treatment times, and bonding and sealing of the X-ray tube to the catheter have not been adequately addressed in the prior art.

SUMMARY OF THE INVENTION

The present invention is a vascular catheter having an X-ray tube as a distal end, sufficiently small and flexible to be inserted through a vein or artery to reach an intended treatment site, such as in the coronary arteries of a patient. The X-ray catheter is capable of delivering X-ray radiation of sufficient power to treat the vascular walls to prevent restenosis, particularly following balloon angioplasty. In the X-ray tube itself, the walls are highly insulative and at the same time highly transmissive to X-ray radiation. The level of X-ray radiation is sufficient to achieve the needed radiation dosage within a short period of time, such as within ten minutes.

In a preferred embodiment of the invention, a vascular X-ray catheter comprises a flexible optical fiber having a bore through its length, a first electrical conductor extending through the bore of the fiber, a second conductor on the outer surface of the fiber, and an essentially cylindrical tube formed of insulative and X-ray transmissive material secured on the distal end of the optical fiber. The tube has a proximal end secured in sealed connection to the outer wall of the fiber, at a position slightly back from the end of the fiber, and the tube has a distal end, thus defining a vacuum chamber within the tube. A cathode is secured to the end of the optical fiber within the tube, the cathode being electrically connected to the first conductor in the bore of the fiber. The cathode is a thermionic cathode, excitable by heat to emit electrons. Within the tube and near its distal end, an anode is positioned, the anode comprising a target for emitting X-rays when bombarded by electrons. At the proximal end of the optical fiber is an optical radiation emitting device, such as a diode laser, for delivering optical radiation through the optical fiber of sufficient power to heat the cathode so as to emit electrons.

In a preferred embodiment the diameter of the tube, which is greater than that of the optical fiber, is no greater than about 1.5 mm.

The invention also encompasses a method of use of the vascular catheter, for preventing restenosis within the lumen of a vascular element of a patient, particularly following angioplasty. The method includes advancing the X-ray catheter through the patient's lumen to a desired location at a site of the lumen to be treated, then activating an X-ray tube at the tip of the catheter by directing optical radiation through the flexible catheter shaft, which comprises an optical fiber, while also establishing through conductors carried by the catheter an electrical potential between a cathode and an anode within the X-ray tube. The cathode is secured to the end of the optical fiber and comprises a thermionic cathode, emitting electrons when excited by heat resulting from the optical radiation impinging on the cathode. According to the method the X-ray tube is activated for a period of time effective to deliver an appropriate dose of X-ray radiation to the vessel wall to prevent or retard restenosis. The X-ray tube is then deactivated and the catheter is removed.

It is thus among the objects of the invention to effectively treat human blood vessels by radiation to discourage or prevent restenosis after a treatment such as angioplasty, using a small-diameter catheter which comprises an optical fiber with a small-diameter X-ray tube at its end, the fiber providing a path for delivering optical radiation to a thermionic cathode; and to provide such an X-ray catheter capable of delivering an effective, switchable dose of X-ray radiation. These and other objects, advantages and features of the invention will be apparent from the following description of preferred embodiments, considered along with the accompanying drawings.

DESCRIPTION OF THE PREFERRED EMBODIMENT

Figure 1:
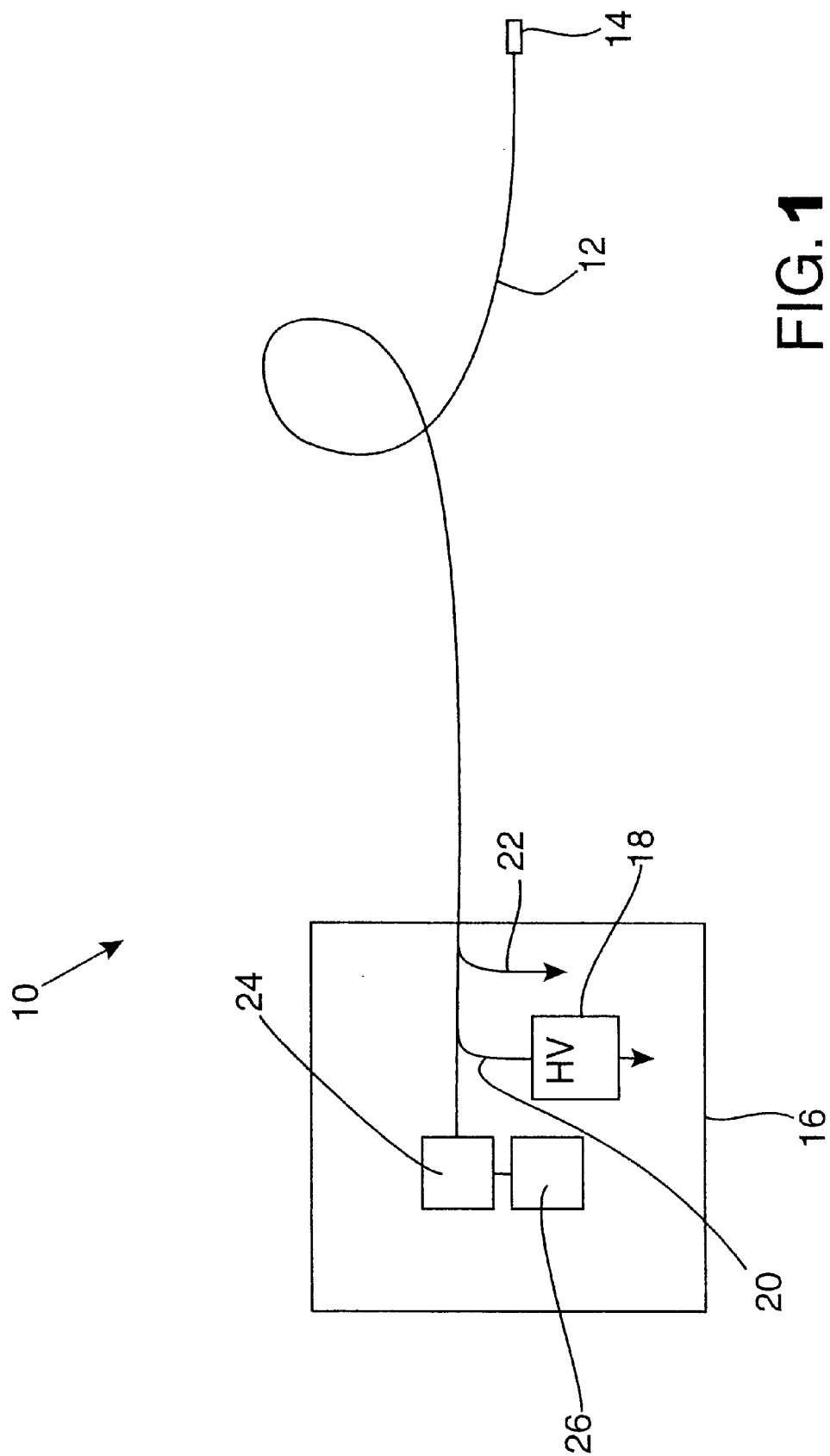
FIG. 1 is a schematic system diagram illustrating a vascular probe and a power supply/control module.

FIG. 1 shows a vascular pro be system 10, including an elongated flexible probe cable 12 with an X-ray tube 14 at its end. The drawing also shows a system power supply and control module 16, which includes a high voltage supply 18, with a voltage control, a high voltage lead 20 extending into the flexible probe cable 12, a ground line 22 extending into the flexible probe cable, a source of optical radiation 24, preferably a diode laser, and a power supply 26 for the optical radiation device. Optical radiation is directed through the flexible probe cable 12, which includes an optical fiber, and is delivered to the proximal end of the X-ray tube 14 to heat a thermionic cathode therein, as explained below. The tube 14 preferably includes an appropriate form of centering device, which may be mechanical, for centering the tube in the vessel lumen.

Figure 2:
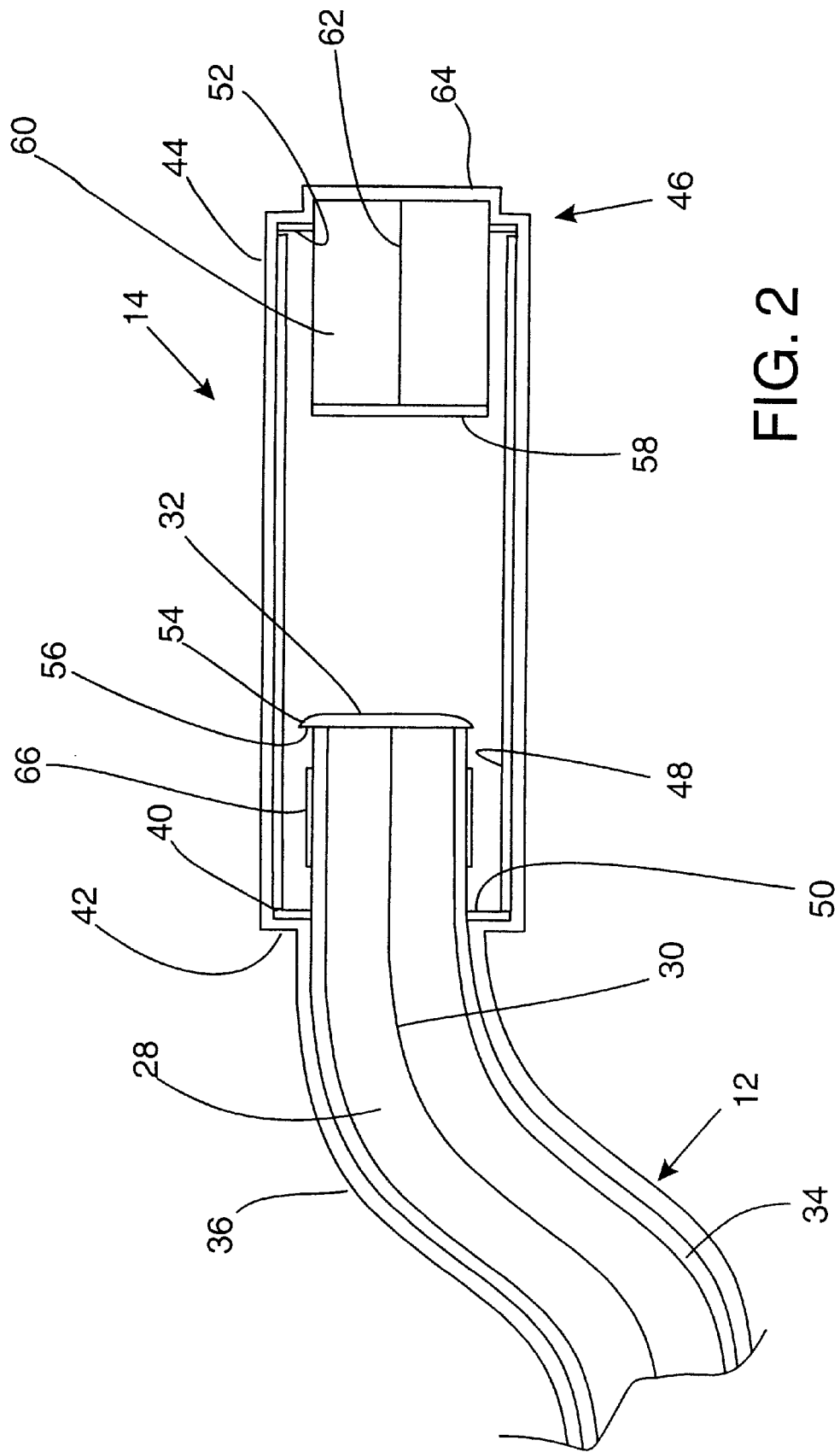
FIG. 2 is a cross sectional view showing a distal end of the vascular probe with an X-ray tube, in a first embodiment.

FIG. 2 shows schematically in a cross sectional view the flexible probe cable 12, which in this preferred embodiment comprises an optical fiber 28 having embedded within it a high voltage conductor 30. This assembly can be produced by using a glass fiber with a central bore within which is inserted or deposited the conductor 30, and the fiber can be heated and drawn to shrink the bore onto the conductor 30, if the conductor comprises a wire. In a preferred embodiment the optical fiber 28 is a quartz fiber, which is highly transmissive for infrared radiation and which is strong and highly resistant to breakage on bending, giving the fiber a small radius for maximum curvature. The conductor 30 through the center of the hollow fiber can be thin wire, metal paints, evaporated metal films or conductive fluids. A wire can be fed through the fiber's bore and left, or a wire can be fed through the bore and flashed (by passing a large current through the wire to evaporate it), metal paint can be forced through the bore and then fired to cure the paint into a conductive layer, or the tube could be evacuated and a conductive fluid introduced to fill by capillary action. This latter approach is novel and ensures that a conductive path is made after the tube is sealed and tested. This conductor need not carry more than 100 to 400 microamps of current. If the tube operates at 20 kV, then the resistance of the conductor needs to be less than $10^{-9}$, which is easily accomplished.

The wire or conductor 30 is connected to a cathode 32, preferably mounted directly on its end as shown. The cathode is a thermionic cathode, heated by the optical radiation, preferably a laser beam and advantageously an infrared beam. The cathode generally is made from a low work function material such as tungsten, or from materials such as nickel 200 preferably coated with a metal oxide powder such as thoria or yttria. To allow it to heat with little energy, the cathode should be very thin.

On the outer surface of the flexible probe cable 12 is a first coating 34, a total internal reflection coating such as typically used on communications fibers. An outer coating layer 36 shown over the coating 34 is a second electrical conductor, preferably comprising a ground covering over the optical fiber. The conductor coating 36 can be aluminum, or another higher temperature good electrical conductor.

The X-ray tube 14 is secured at the end of the flexible optical fiber cable 12, as schematically shown in FIG. 2. The conductor coating 36 from the optical fiber essentially continues over a proximal end 40 of the tube, as shown at 42, and over the sides of the tube at 44, to a distal end 46 of the tube. This conductive coating 42, 44 can be applied by evaporative or sputter coating onto the tube. The coating can be extremely thin, e.g. approximately 0.1 micron.

The X-ray tube 14, which is preferably cylindrical in shape, is formed of a material which is highly insulative and also highly transmissive to X-ray radiation. This is particularly true of the wall 48 of the tube, through which the radiation passes. Materials from which the wall 48 can be made include alumina, sapphire, boron nitride, aluminum nitride and diamond. End plates 50 and 52 at the proximal and distal ends of the tube 14 are of a compatible material or a transition material to accommodate differences in thermal expansion coefficients between the quartz fiber 28 and the X-ray tube wall 48. Joints are made by fusing, as by use of solder glass.

As shown in FIG. 2, the thermionic cathode 32 overlaps the optical fiber 28, with an overhanging annular ledge 54. This shadows the triple junction 56 (the interface where the insulator, conductor and vacuum are in close proximity) at the back of the cathode from the ground, which is an anode 58 at or near the distal end of the X-ray tube 14.

As also shown in FIG. 2, the optical fiber 28 extends into the tube 14 a certain distance, forming a standoff for the electrodes 32 and 58. In other words, this creates a longer surface path length between the cathode and the anode, to minimize surface breakdown.

At the distal end, another standoff 60 is provided, as by a cylindrical section of glass bonded to the tube end piece 52 and extending into the tube, toward the cathode. A ground conductor 62 passes through this standoff element 60 and is electrically connected to the anode 58. At the other end of the conductor 62, it connects with the ground conductive coating, shown at 64 on the distal end of the device and connected to the other elements of the coating 44 and 42.

The anode 58 comprises an X-ray producing target for electrons passing between the cathode and the anode in this embodiment, and may be formed of molybdenum, rhenium, tungsten, copper, rhodium, or other typical heavy metal, high Z materials. The target could be separate from the anode if desired, but it is more efficiently combined with the anode. The anode conductor 62 can be similar to the conductor 30, described above.

FIG. 2 also schematically indicates a getter 66 coated onto the exterior of the optical fiber within the X-ray tube 14. Such getters are well known, to counteract any release of molecules into the high vacuum chamber in the interior of the tube 14.

Figure 4:
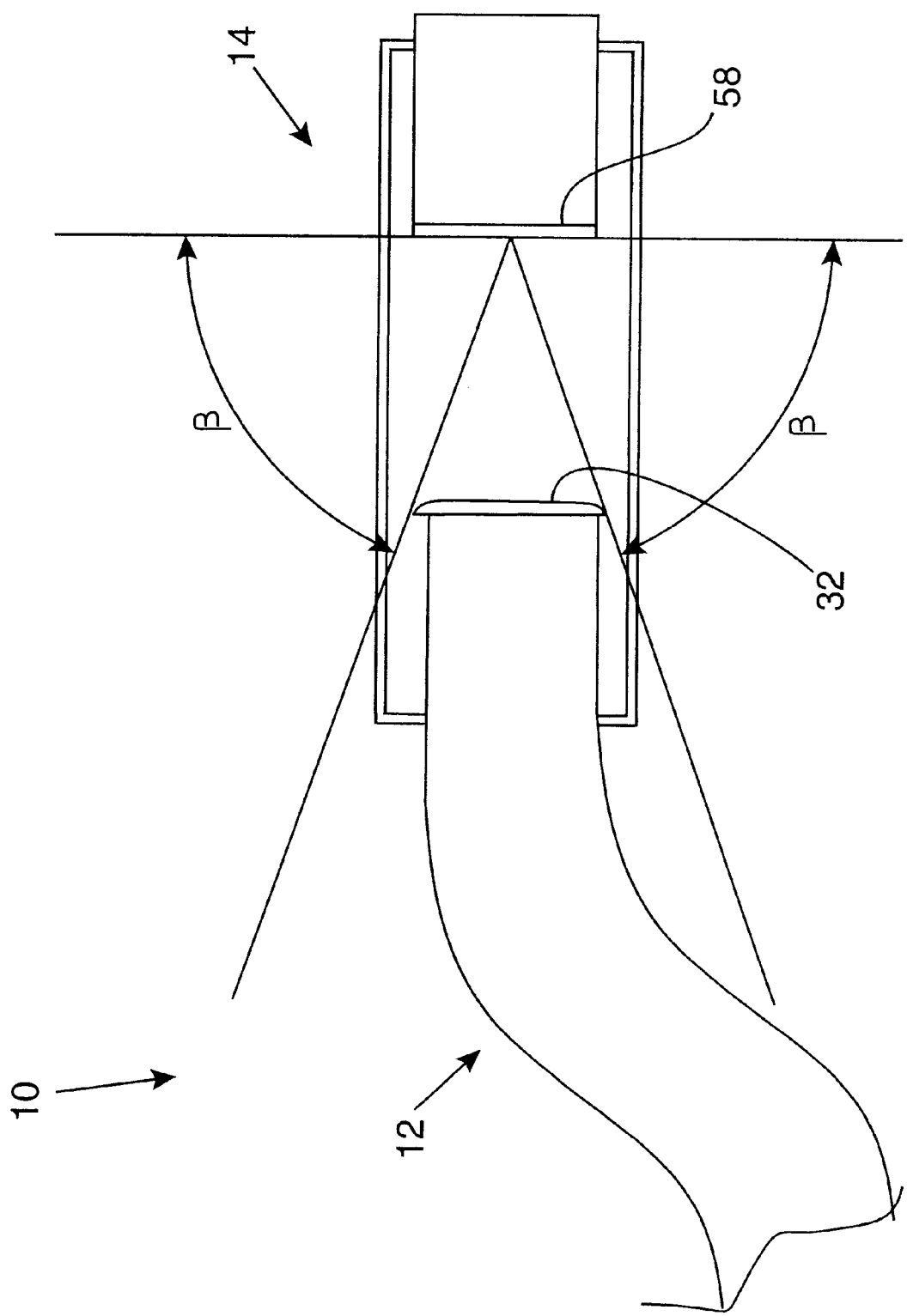
FIG. 4 is a view partially in cross section, indicating an approximate pattern of X-ray radiation emanating from the X-ray tube of FIG. 2.

FIG. 4 shows schematically, and without details of construction, an approximate pattern of radiation generated by the vascular probe device 10 with an X-ray tube 14 as shown in FIG. 2. The anode 58, comprising the photon-emitting electron target for the tube, is too thick to be penetrated by the electrons traveling from the cathode and bombarding the anode, nor can photons issued from this bombardment escape through the back side of the anode/target 58 because of the large amount of material behind the anode for supporting the anode and to assist in removing heat generated at the anode. Also, the cathode 32 limits the angular range of photon emission back toward the left as seen in the figure. Thus, the angle of treatment range is approximately the angle beta indicated in the drawing, being in an approximate range of about 60 to 80 degrees, depending on the sizes of the cathode and anode and their proximity.

Figure 3:
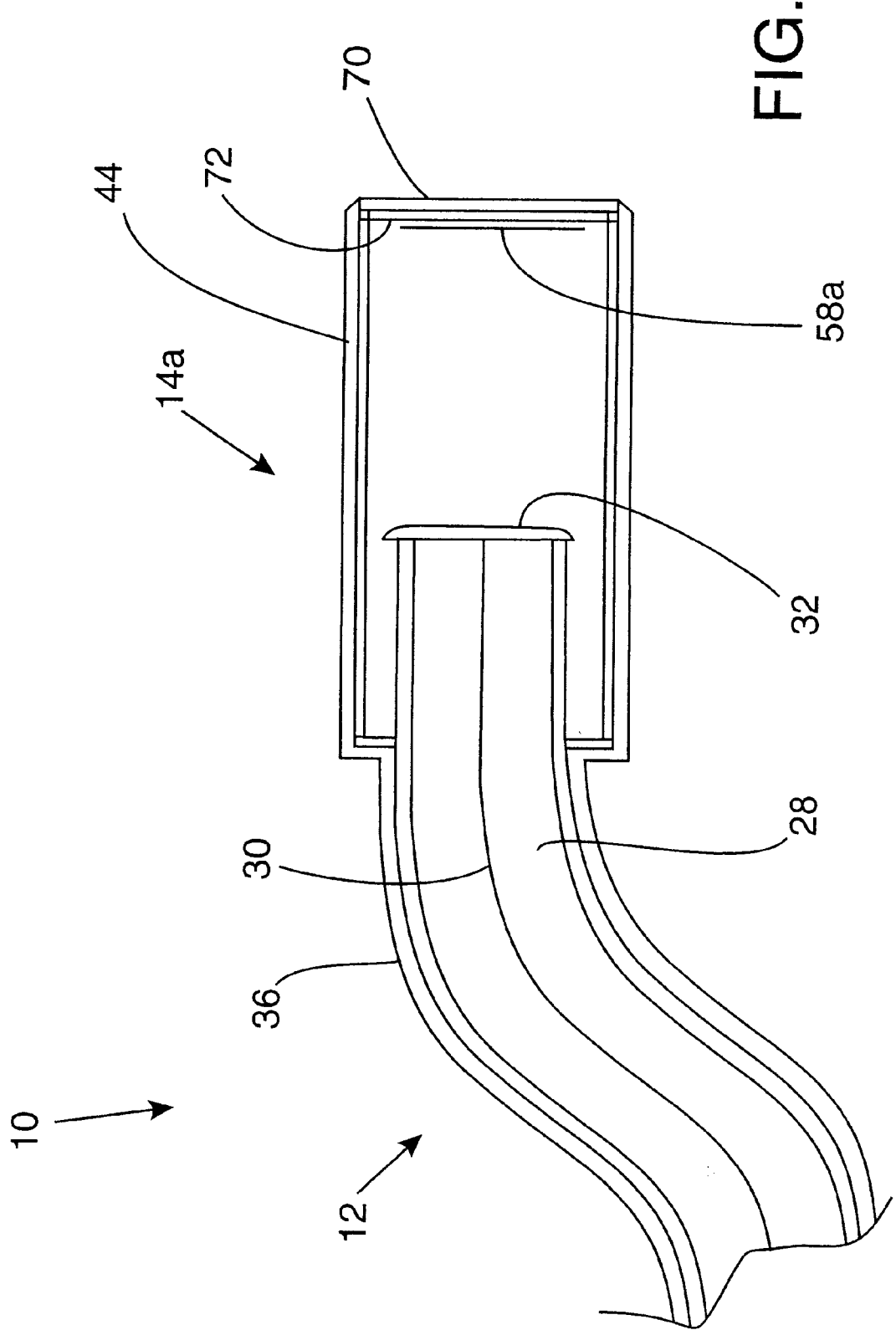
FIG. 3 is a view similar to FIG. 2, showing a different embodiment of an X-ray tube.

FIG. 3 shows a vascular probe device 10 with a similar vascular probe cable 12 but a different form of X-ray tube 14*a*. This form of X-ray tube has a cathode 32, optical fiber 28, high voltage conductor 30 and external ground conductor 36 similar to those described relative to FIG. 2, but has an anode at an end window 70. The end window, which is preferably a good heat conductor, low Z material, also vacuum compatible and sealable, may be diamond, beryllium, sapphire, boron nitride, boron carbide, or other such materials used in X-ray tubes. The anode for this tube is shown at 58*a*, and is a very thin layer of an anode/X-ray target material such as tungsten, molybdenum or other materials discussed above. The layer which comprises the anode/target 58*a* may be deposited or sputtered on the window, but preferably a first layer 72 is deposited onto the window as an electrical conductor to the exterior conductor 44 of the tube. This forms a conductive path from the target 58*a* through the conductive layer 72 to the exterior conductor layer 44, grounding the anode.

Figure 5:
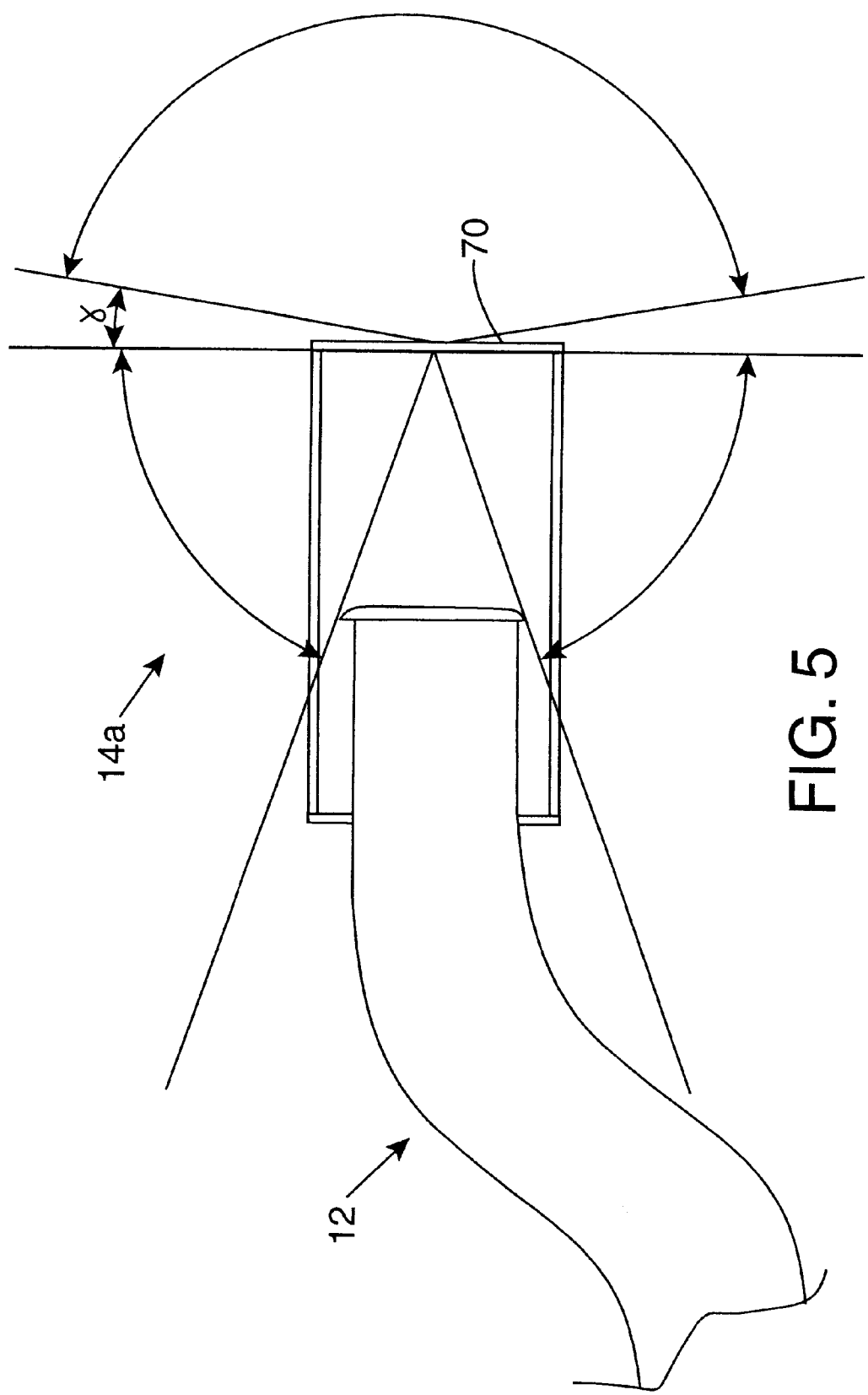
FIG. 5 is a view similar to FIG. 4, but showing an approximate pattern of X-ray radiation which emanates from the X-ray tube shown in FIG. 3.

With the window 70 formed of a material with low X-ray attenuation, such as the materials described above, and with the anode/target sufficiently thin so as not to block radiation, a radiation treatment patter n such as shown in FIG. 5 can be achieved with the X-ray tube 14*a*. As seen in the approximate pattern shown, only a small angle γ is effectively shadowed from the release of photons as X-ray radiation from the anode/target. This minor shadowing is due to the thickness of the window 70 in the lateral direction.

Figure 6:
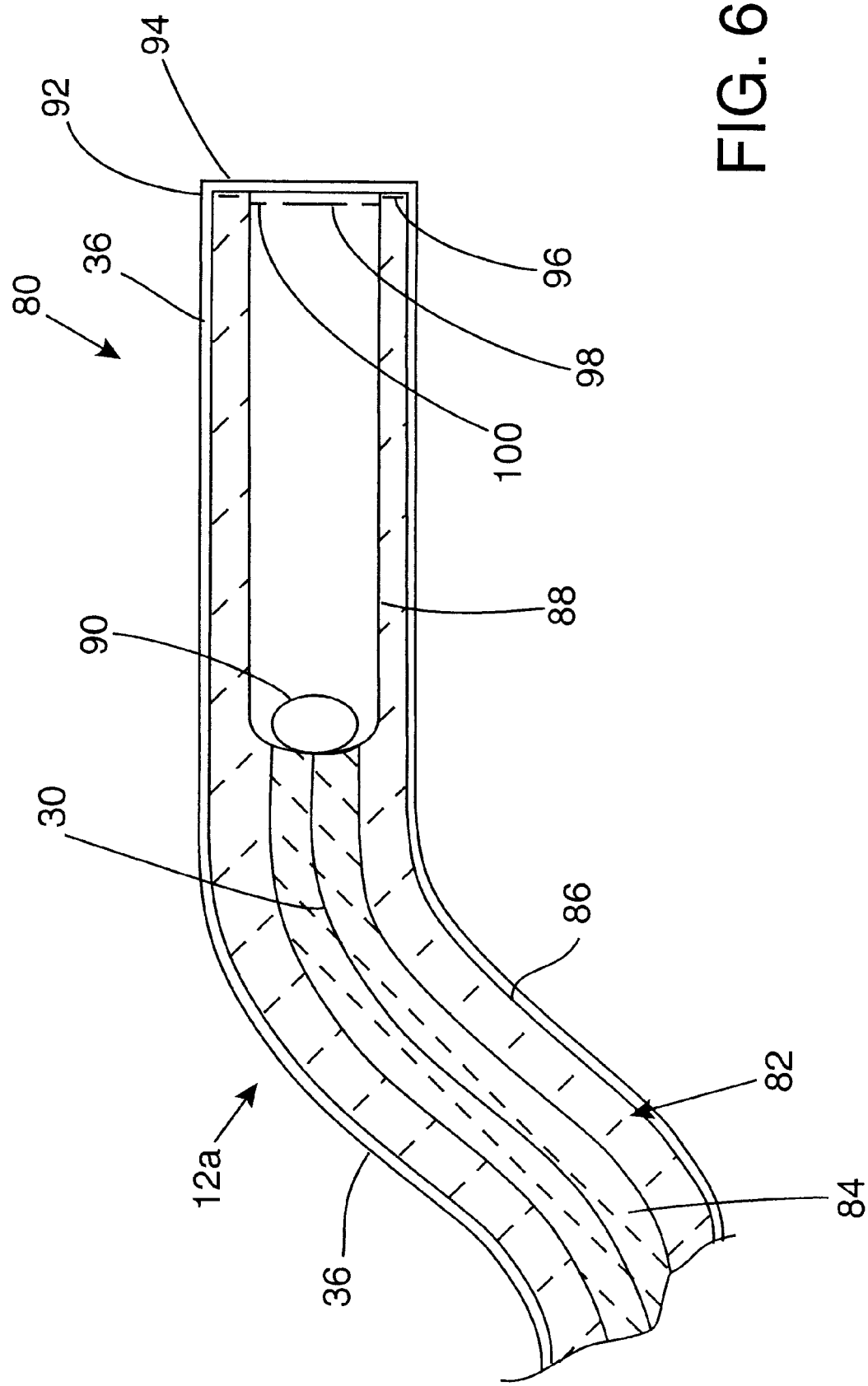
FIG. 6 is a view showing another embodiment of an X-ray tube formed in the end of the probe cable.

FIG. 6 shows another preferred embodiment of the invention, wherein an X-ray tube 80 is formed as a part of the flexible vascular probe cable 12*a* of the system. In this form of the invention, an optical fiber 82 is composed of an inner light conduit fiber 84 through which the optical radiation is delivered, and a total reflective coating 86, of slightly different glass or glass-like material, which is formed over the core conduit 86 and which, in this embodiment, occupy as much of the volume of the cable 12*a*. The X-ray tube is formed at 88, bored or oblated out of the composite optical fiber 82, as by milling with diamond drills or ultrasonic drilling. The reason for the narrower optical radiation conduit 84 in this embodiment is to direct that radiation essentially only at the cathode 90 which is positioned at the proximal end of the X-ray tube, and electrically connected to the wire or conductor 30 embedded within the core fiber 84. If the core fiber were of larger diameter as in the embodiments of FIGS. 2–5, much of the optical radiation energy would be dispersed around the outside of the X-ray tube 88.

The exterior of the vascular probe cable 12*a* has a coating similar to the embodiments described above, i.e. a shielding ground conductor coating 36 which covers the entire probe to its end 92, at the distal end of the X-ray tube 88. There the fiber optic tubular end, which may be formed only from the outer, total reflective coating material 86 as shown in FIG. 6, is joined to an end window 94 which may be similar to and formed of similar materials, as the end window 70 described relative to FIG. 3. If the window material has a different expansion coefficient than the tube body, an intermediate material may be needed, with an intermediate expansion coefficient. As in the embodiment of FIG. 3 and 5, the end window 94 has an inner coating 96 which provides electrical conductivity from an anode/target 98 out to the ground shield coating 36, thus providing a ground electrical path to the anode. The window 94 itself may be bonded to the optical fiber device 82, 86, which is preferably of quartz, by solder glass or intermediate glass.

In this embodiment a getter material may be applied in an annular pattern 100, surrounding the anode/target 98.

The X-ray radiation pattern generated by the X-ray tube 88 is similar to that shown in FIG. 5, which embodiment also had an end window anode. In this case the cathode 90 will shadow the X-ray photon radiation even less.

In this form of the X-ray tube 88 the cathode does not have a deep standoff from the proximal end of the tube, as was the case with the embodiments of FIGS. 2 and 3. However, to compensate for this, the tube 88 can be made longer, since the tube itself is inherently flexible at least to the degree of the remainder of the vascular probe cable 12*a*, and the flexibility should be even greater due to the presence of the hollowed out X-ray cavity 88. To shadow the triple points of the cathode, the cathode 90 may be shaped as shown.

The vascular probe cable 12*a* with integral X-ray tube 88 has a number of advantages: it is simpler in construction, with the only sealed bonding required at the distal end of the tube, where the end window 94 is bonded to the end of the hollowed-out optical fiber; the X-ray tube is very small in diameter, the same outer diameter as the probe cable 12*a* itself; the X-ray tube is as flexible as the cable 12*a* itself, or more so; due to flexibility the tube 88 can be made as long as needed to provide a lengthy surface path to minimize surface breakdown; the ground conductive path to the anode is deposited directly on the end window, so that the connection is made directly when the window is secured to the fiber; a wide range of pattern for X-ray radiation, as shown in FIG. 5, is easily achieved; there are fewer components within the X-ray tube, minimizing problems of outgassing and virtual leaks; and materials capability problems, regarding expansion coefficients and bonding, are fewer because of the simple construction.

The vascular probe cable 12*a* with the built-in X-ray tube 88 can be less than 3 mm in diameter, and in a preferred embodiment it is less than 2 mm in diameter, preferably about 1.5 mm or even 1.0 mm particularly for the FIG. 6 form of the invention. The internal diameter of the X-ray tube itself should be as large as possible without compromising voltage hold off and necessary wall strength. Tube walls generally can be about 5 mils to 10 mils.

Because the X-ray tube reaches high temperatures in a small space, it may be necessary to provide cooling. An open-ended system can be used, or a closed loop system comprising a thin sheath over the cable and X-ray tube, with passages carrying liquid coolant. Such systems are known in other applications.

The above described preferred embodiments are intended to illustrate the principles of the invention, but not to limit its scope. Other embodiments and variations to this preferred embodiment will be apparent to those skilled in the art and may be made without departing from the spirit and scope of the invention.

I claim:

1. A vascular probe having an X-ray tube as a distal end, comprising:

a flexible optical fiber having a bore through its length, a first electrical conductor extending through the bore of the optical fiber, a second conductor on the outer surface of the optical fiber, an essentially cylindrical tube formed of electrically insulative and X-ray transmissive material secured on a distal end of the optical fiber, the tube having a proximal end secured in a sealed connection to the outer wall of the optical fiber, at a position spaced back from the end of the optical fiber, and the tube having a distal end and defining a vacuum chamber within the tube, a cathode secured to the end of the optical fiber within the tube, the cathode being electrically connected to said first conductor in the bore of the fiber, the cathode comprising a thermionic cathode which is excitable by heat to emit electrons, an anode formed within the tube near its distal end, and an anode conductor connecting said second conductor from the exterior of the optical fiber to the anode, with an X-ray target in the path of electrons moving from the cathode to the anode, optical radiation means at the proximal end of the optical fiber for delivering optical radiation through the optical fiber, of sufficient power to heat the cathode so as to emit electrons, and means for selectively switching electrical power to the cathode and anode to establish a potential between the cathode and anode when desired, to thereby cause X-rays to be emitted outwardly from the tube.

2. A vascular probe according to claim 1, wherein the optical radiation means comprises a diode laser.

3. A vascular probe according to claim 1, wherein said tube is formed of alumina and has a proximal end with a central hole, connected in sealed relationship to the exterior surface of the optical fiber.

4. A vascular probe according to claim 1, wherein the vascular probe is configured such that any triple junctions are shadowed so as to prevent emission of electrons to the cathode.

5. A vascular probe according to claim 1, wherein the diameter of the tube is no greater than about 1.5 millimeters.

6. A vascular probe according to claim 1, wherein the diameter of the tube is about one millimeter.

7. A vascular probe according to claim 1, further including means for controlling the potential between the cathode and the anode to control the level of X-ray output from the tube.

8. A vascular probe according to claim 1, wherein the tube has a proximal end with an opening through which the optical fiber passes, the optical fiber being formed of glass, and wherein the tube is fused together with the exterior surface of the glass optical fiber.

9. A vascular probe according to claim 1, wherein the anode includes the X-ray target.

10. A vascular probe according to claim 1, wherein the X-ray target comprises a coating on the anode.

11. A method for treating the lumen of a blood vessel to discourage restenosis following a PTCA procedure, comprising:

providing a vascular X-ray probe comprising a flexible optical fiber having at its distal end an X-ray tube, the vascular probe being sufficiently small in width to be insertable through the lumen of a human blood vessel, and the X-ray tube having a thermionic cathode positioned at the end of the optical fiber so as to receive optical radiation delivered through the optical fiber to heat the thermionic cathode to emit electrons to an anode and a target within the X-ray tube, and the vascular probe additionally having a pair of conductors for delivering an electrical potential to the anode and the cathode, inserting the X-ray vascular probe through the lumen of a human blood vessel, to a position wherein the X-ray tube is at a site of the lumen to be treated, switching power to the X-ray tube through the conductors and delivering optical radiation through the optical fiber, sufficient to heat the thermionic cathode to emit electrons, the electrons being delivered to the anode and striking the target via the electrical potential, thus emitting X-ray radiation from the X-ray tube in an effective dose to prevent or discourage restenosis within the lumen, switching off power to the X-ray tube to discontinue the radiation, and removing the vascular probe from the patient's blood vessel.

12. A vascular probe having an X-ray tube as a distal end, comprising:

a flexible optical fiber, a first electrical conductor embedded in and extending through the length of the optical fiber, a second conductor on the outer surface of the optical fiber, an X-ray tube formed of electrically insulative material on a distal end of the optical fiber, the tube having a proximal end in sealed relationship with the outer wall of the optical fiber, and the tube having a distal end and defining a vacuum chamber within the tube between the ends of the tube, a cathode at the end of the optical fiber within the tube, the cathode being electrically connected to said first electrical conductor in the fiber, the cathode comprising a thermionic cathode which is excitable by heat to emit electrons, an anode formed with in the tube near its distal end, and an anode conductor connecting said second conductor from the exterior of the optical fiber to the anode, with an X-ray target in the path of electrons moving to the anode, optical radiation means at the proximal end of the optical fiber for delivering optical radiation through the optical fiber, of sufficient power to heat the cathode so as to emit electrons, and means for selectively switching electrical power to the cathode and anode to establish a potential between the cathode and anode when desired, to thereby cause electrons to strike the target to cause X-rays to be emitted from the tube.

13. A vascular probe according to claim 12, wherein the anode includes the X-ray target.

14. A vascular probe according to claim 13, wherein the X-ray target comprises a coating on the anode.

15. A vascular probe according to claim 12, wherein the X-ray tube has a proximal end with an opening through which the optical fiber passes, the optical fiber extending a selected distance into the tube, with the cathode mounted on the distal end of the optical fiber, providing a stand off for the cathode within the tube, increasing effective surface path length to the anode.

16. A vascular probe according to claim 15, further including a stand off mounting on which the anode is secured, holding the anode spaced inwardly from the distal end of the tube and increasing effective surface path length between the anode and the cathode.

17. A vascular probe according to claim 12, wherein the X-ray tube includes an exit window as its distal end, on which the anode is positioned, whereby X-ray radiation is directed in wide arcs out through the X-ray tube and outside the exit window.

18. A vascular probe according to claim 17, wherein the exit window has an interior surface coated with a conductive material, said anode conductor including a conductive coating on the exterior of the X-ray tube, making contact with the conductive coating on the exit window.

19. A vascular probe according to claim 17, further including a getter material deposited in an annulus on the exit window, surrounding the anode.

20. A vascular probe according to claim 12, wherein the X-ray tube comprises a cavity hollowed out of the optical fiber at its distal end.

21. A vascular probe according to claim 20, wherein the X-ray tube includes an exit window secured to the distal end of the hollowed out optical fiber, with the anode mounted on the exit window.

22. A vascular probe according to claim 20, wherein the optical fiber comprises a core fiber material and an outer coating fiber material, the core fiber material being essentially no larger in diameter than the X-ray tube and being positioned to receive the optical radiation, so that the core fiber ends at the proximal end of the X-ray tube and such that the outer coating fiber material forms a cylindrical outer wall of the X-ray tube.

* * * * *